United States Patent [19]

Meguro et al.

[11] 4,116,956
[45] Sep. 26, 1978

[54] BENZODIAZEPINE DERIVATIVES

[75] Inventors: Kanji Meguro; Yutaka Kuwada, both of Hyogo, Japan

[73] Assignee: Takeda Chemical Industries, Ltd., Osaka, Japan

[21] Appl. No.: 718,194

[22] Filed: Aug. 26, 1976

Related U.S. Application Data

[62] Division of Ser. No. 367,766, Jun. 7, 1973, abandoned, which is a division of Ser. No. 874,367, Nov. 5, 1969, abandoned.

[30] Foreign Application Priority Data

| Nov. 5, 1968 [JP] | Japan | 43-80813 |
| Dec. 17, 1968 [JP] | Japan | 43-92928 |
| Dec. 17, 1968 [JP] | Japan | 43-92929 |
| Dec. 17, 1968 [JP] | Japan | 43-92930 |
| Dec. 25, 1968 [JP] | Japan | 43-95187 |
| Feb. 13, 1969 [JP] | Japan | 44-10702 |

[51] Int. Cl.$^2$ .......................... C07D 243/20
[52] U.S. Cl. .......................... 260/239 BD; 424/244
[58] Field of Search .......................... 260/239 BD

[56] References Cited

U.S. PATENT DOCUMENTS 3,751,426 8/1973 Hester .......................... 260/239 BD

OTHER PUBLICATIONS

Hester, Chem. Abstracts, vol. 78, Abst. No. 159693k (1973).
Theilheimer (I), "Synthetic Methods of Org. Chem.," vol. 20, p. 298, Synthesis 356 (1966).
Theilheimer (II), Synthetic Methods of Org. Chem., vol. 16, p. 208, Synthesis 437 (1962).

Primary Examiner—Donald G. Daus
Assistant Examiner—D. B. Springer
Attorney, Agent, or Firm—Wenderoth, Lind & Ponack

[57] ABSTRACT

Benzodiazepine derivatives of the general formula

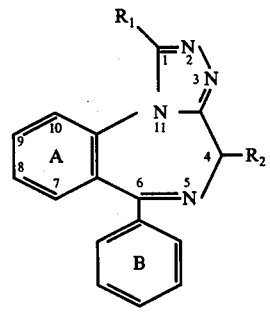

where $R_1$ is hydrogen or a hydrocarbon residue of 1–8 carbon atoms, $R_2$ is hydrogen or lower alkyl and rings A and B are unsubstituted or substituted by nitro, trifluoromethyl, halogen, lower alkyl or lower alkoxy, the nitrogen atom in the 5-position being unsubstituted or substituted by an oxygen atom, useful as muscle relaxants, anticonvulsants, sedatives and tranquilizing agents, and processes for production thereof. Also provided are novel intermediates of the general formula

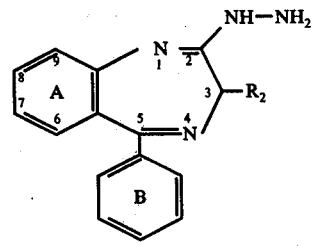

where $R_2$ has the above meaning, rings A and B are unsubstituted or substituted as above and the nitrogen atom in the 4-position is unsubstituted or substituted by an oxygen atom.

2 Claims, No Drawings

BENZODIAZEPINE DERIVATIVES

This application is a divisional of Ser. No. 367,766 filed June 7, 1973 now abandoned, which is a divisional of Ser. No. 874,367 filed Nov. 3, 1969 now abandoned.

This invention relates to novel and useful benzodiazepine derivatives of the general formula

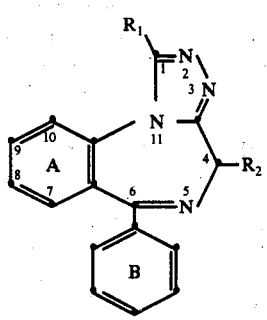
(I)

wherein $R_1$ is hydrogen or a hydrocarbon residue, $R_2$ is hydrogen or lower alkyl and the rings A and/or B are unsubstituted or substituted by one or more of the same or different substitutents selected from nitro, trifluoromethyl, halogen, alkyl and alkoxy groups, including the case where the nitrogen atom at the 5-position carries an oxygen atom.

This invention also relates to a novel and useful process for producing the benzodiazepine derivatives I.

Referring to the general formula I, as the hydrocarbon residue represented by $R_1$, there are mentioned generally those having 1 to 8 carbon atoms, including alkyl of up to six carbon atoms (e.g. methyl, ethyl, propyl, isopropyl, butyl, sec-butyl, amyl, hexyl, tert-butyl, etc.), aralkyl (e.g. benzyl, phenethyl, etc.) and aryl (e.g. phenyl). The lower alkyl represented by $R_2$ is exemplified by methyl, ethyl, propyl, isopropyl, butyl, sec-butyl, tert-butyl, amyl, hexyl, etc. Both rings A and B may be unsubstituted or substituted by one or more of the same or different substituents selected from nitro, trifluoromethyl, halogen (i.e. chlorine, fluorine, bromine and iodine), alkyl such as lower alkyl (e.g. methyl, ethyl, propyl, etc.) and alkoxy such as lower alkoxy (e.g. methoxy, ethoxy, etc.)

The benzodiazepine derivatives I can be produced by reacting a 2-hydrazinobenzodiazepine derivative of the general formula

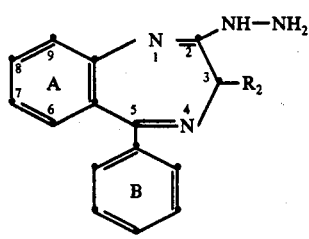
(II)

wherein $R_2$ has the same meaning as defined above and rings A and/or B are unsubstituted or substituted as defined above including the case where the nitrogen atom at the 4-position carries an oxygen atom, with carboxylic acids of the general formula $R_1$-COOH (III)

wherein $R_1$ has the same meaning as defined above, or their reactive derivatives. The reactive derivatives of the carboxylic acids III are exemplified by esters (e.g. alkylesters such as lower alkylesters, e.g. methyl and ethyl esters, or activated esters such as p-nitrophenyl ester), anhydrides (e.g. of lower alkyl carboxylic acids), halogenides (e.g. fluoride, chlo iodide and bromide), amides (e.g. of lower alkyl carboxylic acids, such as formamide, dimethylformamide, acetamide), orthoesters, iminoethers and amidines.

The orthoesters are illustrated by the general formula $R_1C(OR_3)_3$ (III')

wherein $R_1$ has the same meaning as defined above and $R_3$ is lower alkyl such as methyl and ethyl.

The iminoethers are illustrated by the general formula

(III")

wherein $R_1$ and $R_2$ have the same meaning as defined above.

The amidines are illustrated by the general formula

(III''')

wherein $R_1$ has the same meaning as defined above.

The carboxylic acids III or their reactive derivatives are employed generally in an amount of about 1 to about 10 moles, preferably in an amount of about 2 to about 5 moles per mole of 2-hydrazinobenzodiazepine derivative II. The reaction is preferably carried out in the presence of a solvent and an acid catalyst at a temperature generally between about 0° to about 300° C, but the conditions vary with the reagents used. The solvents are exemplified by methanol, ethanol, chloroform, methylene chloride, dimethylformamide and mixtures thereof. The acid catalyst is exemplified by inorganic acids (e.g. hydrochloric acid, sulfuric acid, phosphoric acid, polyphosphoric acid, etc.), organic carboxylic acids (e.g. acetic acid, propionic acid, etc. ) and organic sulfonic acids (e.g. benzenesulfonic acid, p-toluene sulfonic acid, etc.). The amount of acid catalyst utilized is generally about 2 moles to about 10 moles per mole of 2-hydraziobenzodiazepine derivative II.

In this reaction, acylhydrazine compounds IV, their enolether derivatives IV' or α-aminoalkylidene (or aralkylidene) compounds IV" of the general formulae

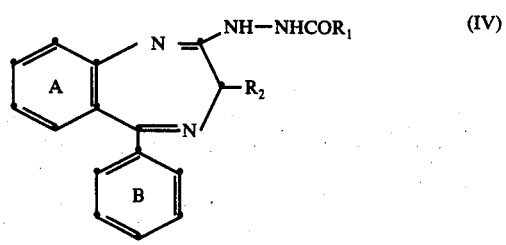
(IV)

-continued

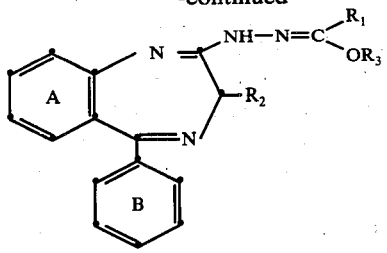

(IV')

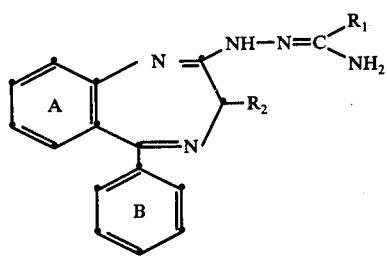

(IV")

wherein the symbols $R_1$, $R_2$, $R_3$, A and B have the same meaning as defined above, including the case where the nitrogen atom at the 4-position carries an oxygen atom, are produced as intermediates. These intermediates can be cyclized to the compounds I under somewhat drastic conditions. In the present method, the compound I may be synthesized in one step without isolating the intermediates, or alternatively, may be synthesized in two steps by producing and isolating the intermediates and then allowing them to cyclize to the compound I.

For instance, when amidines are used under mild conditions, e.g. in a solvent at about room temperature, the intermediate IV''' can be isolated. The intermediate IV''' can then be cyclized on heating at about 140° C to 250° C to the compound I while generating ammonia. Therefore, for the one step synthesis of the compounds I, the 2-hydrazinobenzodiazepine derivatives II and amidines III''' are preferably allowed to react with each other at a rather high temperature, e.g. about 140° C to 250° C. This reaction proceeds either in the presence or absence of a solvent. Generally, a fusion method, especially in the presence of 2-methylimidazole, gives good results.

Also, when using esters, amides, anhydrides and halogenides, the intermediate, i.e. acylhydrazinebenzodiazepine derivative IV can be isolated if the reaction is conducted under mild conditions, e.g. in a solvent at about room temperature. Thus produced and separated acylhydrazinobenzodiazepine derivatives IV are easily cyclized to the compounds I on heating at about 130° C to 250° C. The cyclization can, if necessary, be accelerated by using a catalyst such as polyphosphoric acid. The cyclization is conducted either in the presence or absence of a solvent. The solvents are exemplified by pyridine, dimethylformamide, xylene or tetralin. As to the intermediate IV', the above-mentioned disclosure is similarly applicable.

Thus produced benzodiazepine derivatives I can be isolated in the form of a free base or suitable acid salt (e.g. chloride, sulfate, acetate, etc.) in a per se conventional manner. For example, the reaction mixture is neutralized with a saturated aqueous solution of sodium bicarbonate and extracted with a suitable solvent (e.g. methylene chloride, chloroform, etc.), followed by distillation of the solvent, whereby the benzodiazepine derivatives I are obtained.

The structure of the benzodiazepine derivatives I is determined from the result of X-ray analysis of 8-chloro-6-phenyl-4H-s-triazolo[4,3-a] [1,4]benzodiazepine.

When the benzodiazepine derivatives I carry an oxygen atom at the 5-position (i.e. 5N-oxides), such compounds can, if necessary, be reduced to the corresponding benzodiazepine derivative I wherein the nitrogen atom at the 5-position carries no oxygen atom. The reduction can be conducted by conventional means, which are exemplified by catalytic hydrogenation and by reduction using halogenophosphorus compounds (e.g. phosphorus trichloride). The hydrogenation is usually carried out in a suitable solvent such as methanol or ethanol at about room temperature and under atmospheric pressure. The reduction using halogenophosphorus compounds can usually be effected upon heating in a suitable solvent such as chloroform or methylene chloride.

The 2-hydrazinobenzodiazepine derivatives II to be employed as the starting material of the above ring closure reaction are novel compounds and can be produced by reacting a 2-aminobenzodiazepine of the general formula

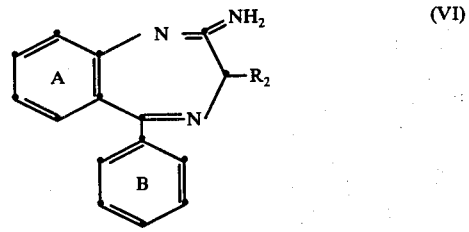

(VI)

wherein the symbols $R_2$, A and B have the same meaning as defined above, including the case where the N-atom at the 4-position carries an oxygen atom, with hydrazine.

Referring to the above general formula VI, the 2-aminobenzodiazepine derivatives may be of the isomeric form

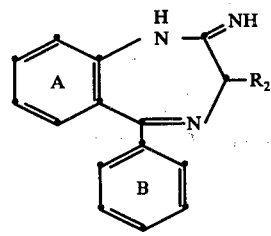

which can also be used in this process.

The compounds of formula VI may be prepared, for example, in the manner described in Journal of Organic Chemistry, 26, 1111 (1961), or by a method which comprises reacting a 2-aminobenzophenone derivative with an alkylamine to produce a 2-amino-α-phenylbenzylidene alkylamine derivative, reacting the 2-amino-α-phenylbenzylidene alkylamine derivative with an aminoacetonitrile derivative and subjecting the resultant 2-amino-α-phenylbenzylideneaminoacetonitrile derivative to cyclization in the presence of an acid or alkali.

The reaction between the 2-aminobenzodiazepine derivative VI and hydrazine is preferably conducted in the presence of a suitable solvent and an acid at an appropriate temperature between about 0° C and about 150° C. The solvents are exemplified by methanol, ethanol, pyridine, dimethylformamidie, mixtures thereof and their aqueous mixtures. The acids are exemplified by inorganic acids (e.g. hydrochloric acid, sulfuric acid, phosphoric acid, etc.) and organic acids (e.g. acetic acid, p-toluenesulfonic acid, etc.). The acids can be added in the form of salts with amines which are exemplified by pyridine, trialkylamines, 2-methylimidazole, etc. It is to be noted that either or both of the hydrazine and 2-aminobenzodiazepine derivative VI can be utilized in the form of their acid salts, and in such case it is not always necessary to add additional acid or amine salt to the reaction system. The amount of hydrazine and acid to be used is generally about one mole to about five moles per mole of 2-aminobenzodiazepine derivative VI, but may be varied to any desired extent, if required.

The 2-hydrazinobenzodiazepine derivatives II produced above can be subjected to subsequent ring closure reaction with or without isolation from the reaction mixture. The isolation of the 2-hydrazinobenzodiazepine derivatives II can be effected by conventinal means, for example, by adding water to the reaction mixture and extracting the mixture with a suitable solvent (e.g. methylene chloride, chloroform, etc.), followed by evaporation of the solvent.

The 2-hydrazinobenzodiazepine derivatives II wherein the nitrogen atom at the 4-position carries no oxygen can also be produced by a process which comprises allowing the compound of the general formula

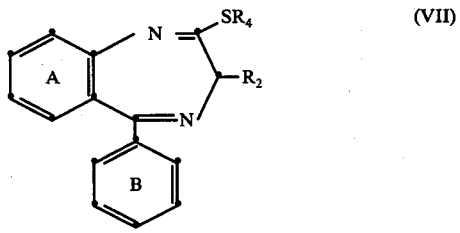

(VII)

wherein $R_2$, A and B have the same meaning as defined above and $R_4$ represents hydrogen, alkyl or aralkyl to react with hydrazine.

Referring to the above general formula VII, when $R_4$ is hydrogen, the compounds may be of the isomeric form

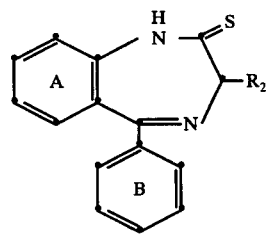

which can also be used in this process.

The compound of the formula VII may be prepared, for example, according to the method described in *Journal of Organic Chemistry*, 29, 231 (1964).

The alkyl represented by $R_4$ is preferably alkyl having up to six carbon atoms such as methyl, ethyl, propyl, isopropyl, butyl, sec-butyl, tert-butyl, amyl, hexyl, etc. The aralkyl represented by $R_4$ is preferably lower aralkyl such as benzyl, phenethyl, etc.

The reaction is generally conducted in the presence of a solvent (e.g. methanol, ethanol, aqueous mixtures thereof, etc.) at about room temperature or under heating, if necessary, at about the boiling point of the solvent used. The amount of hydrazine utilized is about one to about ten moles per mole of compound VII for practical purposes.

The 2-hydrazinobenzodiazepine derivatives II thus produced can be isolated by conventional means, for example, by evaporation of the solvent from the reaction mixture.

The benzodiazepine derivatives I of the present invention, which are novel compounds, show muscle relaxant, anticonvulsant, sedative and taming effects and therefore are useful as muscle relaxants, anticonvulsants, sedatives, tranquilizing agents, etc.

The benzodiazepine derivatives I as well as their acid salts are orally or parenterally administrable per se or in a suitable form such as a powder, granule, tablets or injection solution admixed with a pharmaceutically acceptable carrier or adjuvant. The dose of benzodiazepne derivative I or its acid salt to be administered varies depending on the particular benzodiazepine derivative I, severity of disease, etc., but generally falls within a range of about 1 to about 30 milligrams for oral administration, and about 0.5 to about 10 milligrams for parenteral administration for a human adult per day.

For a further detailed description of the invention, the following examples are given, wherein the term "part(s)" means "weight part(s)" unless otherwise specified, and the relationship between "part(s)" and "part(s) by volume"correspond to that of gram(s) and millilieter(s).

EXAMPLE 1

To a suspension of 3.4 parts of 2-amino-7-chloro-5-phenyl-3H-1,4-benzodiazepine dihydrochloride in 60 parts by volume of methanol is added 1.25 parts of 80% hydrazine hydrate. The suspension is stirred for 40 minutes, diluted with water and extracted with methylene chloride. The extract is washed with water and dried over anhydrous sodium sulfate, followed by evaporation of the solvent. The residue is recrystallized from a mixture of methylene chloride and benzene to give 7-chloro-2-hydrazino-5-phenyl-3H-1,4-benzodiazepine as colorless prisms. Melting point: around 170° C (browning), 202° C to 204° C (decomposition).

Elementary analysis $C_{15}H_{13}ClN_4$: Calculated: C 63.27, H 4.60, N 19.68 Found: C 63.43, H 4.48, N 19.27.

EXAMPLE 2

To a suspension of 3 parts of 2-amino-7-chloro-5-(p-methoxyphenyl)-3H-1,4-benzodiazepine in a mixture of 50 parts by volume of methanol and 0.6 part by volume of glacial acetic acid is added dropwise with stirring 1.5 parts by volume of 100% hydrazine hydrate. The mixture is stirred for 30 minutes and poured into ice water, followed by extraction with chloroform. The chloroform layer is washed with water, dried over sodium sulfate and the solvent is evaporated. Treatment of the residue with benzene yields 7-chloro-2-hydrazino-5-(p-methoxypheyl)-3H-1,4-benzodiazepine as colorless crystals melting at 214° C to 220° C.

Elementary analysis $C_{16}H_{15}ClN_4O$: Calculated: C 61.05, H 4.80, N 17.80 Found: C 60.93, H 4.67, N 17.83.

EXAMPLE 3

To a mixture of 2.35 parts of 2-amino-5-phenyl-3H-1,4-benzodiazepine, 50 parts by volume of ethanol and 1.2 parts by volume of glacial acetic acid is added 1.5 parts by volume of 100% hydrazine hydrate and the mixture is stirred for 1 hour at room temperature. Treatment of the mixture in a similar manner to Example 2 yields 2-hydrazino-5-phenyl-3H-1,4-benzodiazepine as white crystals. Recrystallization from a mixture of methylene chloride and benzene yields white crystals melting at 116° to 118° C. (effervescence).

Elementary analysis $C_{15}H_{14}N_4.1/3\ C_6H_6$: Calculated: C 73.89, H 5.84, N 20.28 Found: C 73.86, H 5.47, N 20.44.

EXAMPLE 4

To a mixture of 9.1 parts of 2-amino-5-phenyl-7-trifluoromethyl-3H-1,4-benzodiazepine, 150 parts by volume of ethanol and 3.6 parts by volume of glacial acetic acid is added 4.5 parts by volume of 100% hydrazine hydrate. The whole mixture is stirred for 30 minutes at room temperature and treated in a similar manner to Example 1, whereby 2-hydrazino-5-phenyl-7-trifluoromethyl-3H-1,4-benzodiazepine is yielded as a crystalline powder. Melting point: 127° C (sintering), 133° C to 135° C (effervescence).

Elementary analysis $C_{16}H_{13}F_3N_4$: Calculated: C 60.37, H 4.12, N 17.60 Found: C 60.05, H 3.96, N 17.40.

EXAMPLE 5

To a mixture of 2.5 parts of 2-amino-7-methyl-5-phenyl-3H-1,4-benzodiazepine, 100 parts by volume of methanol and 1.2 parts of glacial acetic acid is added 2.5 parts of 100% hydrazine hydrate. The mixture is stirred for 1 hour at room temperature and treated in a similar manner to Example 1, whereby 2-hydrazino-7-methyl-5-phenyl-3H-1,4-benzodiazepine is yielded as crystals. Recrystallization from a mixture of chloroform and diethyl ether affords colorless crystals melting at 240° C to 241° (decomposition).

Elementary analysis $C_{16}H_{16}N_4$: Calculated: C 72.70, H 6.10, N 21.20 Found: C 72.70, H 6.08, N 21.31.

EXAMPLE 6

To a mixture of 26.5 parts of 2-amino-7-methoxy-5-phenyl-3H-1,4-benzodiazepine, 500 parts by volume of methanol and 1.2 parts of glacial acetic acid is added 25 parts of 100% hydrazine hydrate. The mixture is stirred for 1 hour at room temperature and treated in a similar manner to Example 1, whereby 2-hydrazino-7-methoxy-5-phenyl-3H-1,4-benzodiazepine is yielded as crystals melting at 110° C to 120° C.

EXAMPLE 7

To a mixture of 5.6 parts of 2-amino-7-nitro-5-phenyl-3H-1,4-benzodiazepine, 200 parts by volume of ethanol and 2.4 parts by volume of glacial acetic acid is added with stirring 5 parts by volume of 80% hydrazine hydrate. The mixture is stirred for 30 minutes at room temperature and treated in a similar manner to Example 1, whereby 2-hydrazino-7-nitro-5-phenyl-3H-1,4-benzodiazepine is yielded as reddish, viscous oily substance.

EXAMPLE 8

To a solution of 16 parts of 2-amino-7-chloro-3-isobutyl-5-phenyl-3H-1,4-benzodiazepine and 25 parts of 100% hydrazine hydrate in 400 parts by volume of methanol is added 6 parts of glacial acetic acid with stirring and ice-cooling. Then the whole mixture is stirred for 5 hours at room temperature. Water is added to the reaction mixture, followed by extraction with chloroform. The chloroform layer is washed with water, dried over sodium sulfate and the solvent is evaporated. Treatment of the residue with isopropyl ether yields 7-chloro-2-hydrazino-3-isobutyl-5-phenyl-3H-1,4-benzodiazepine as colorless crystals melting at 165° C to 168° C.

Thus obtained product is identical with the product prepared in Example 11.

EXAMPLE 9

To a solution of 2 parts of 7-chloro-2-methylmercapto-5-phenyl-3H-1,4-benzodiazepine in 70 parts by volume of ethanol is added 5 parts by volume of 80% hydrazine hydrate and the mixture is allowed to stand at room temperature for 3 days. After evaporation of the solvent, a small amount of water is added to the residue, whereby 7-chloro-2-hydrazino-5-phenyl-3H-1,4-benzodiazepine is obtained as crystals. Recrystallization from a mixture of methylene chloride and benzene gives crystals. Melting point; 175° C (browning), 205° C to 207° C (decomposition).

Thus obtained product is identical with the product prepared in Example 1.

EXAMPLE 10

To a solution of 2.9 parts of 7-chloro-1,3-dihydro-5-phenyl-2H-1,4-benzodiazepine-2-thione in a mixture of 2.5 parts by volume of dimethylsulfoxide and 100 parts by volume of ethanol is added 5 parts by volume of 80% hydrazine hydrate, and the mixture is allowed to stand for 24 hours. After evaporation of the solvent under reduced pressure, the residue is diluted with water, followed by extraction with methylene chloride. The methylene chloride layer is dried over sodium sulfate and the solvent is evaporated. Treatment of the residue with benzene gives 7-chloro-2-hydrazino-5-phenyl-3H-1,4-benzodiazepine. Recrystallization from a mixture of methylene chloride and benzene gives crystals melting at 205° C to 207° C (decomposition) which are confirmed to be identical with the product prepared in Examples 1 and 9.

EXAMPLE 11

To a solution of 1.6 parts of 7-chloro-3-isobutyl-2-methylmercapto-5-phenyl-3H-1,4-benzodiazepine in 150 parts by volume of methanol is added 40 parts of 100% hydrazine hydrate. The mixture is refluxed for 4.5 hours and poured into water, followed by extraction with chloroform. The chloroform layer is washed with water, dried over sodium sulfate and the solvent is evaporated. Treatment of the residue with diethyl ether yields 7-chloro-2-hydrazino-3-isobutyl-5-phenyl-3H-1,4-benzodiazepine as crystals. Recrystallization from a mixture of chloroform and n-hexane yields colorless crystals melting at 168° C to 169° C.

Elementary analysis $C_{19}H_{21}ClN_4$: Calculated: C 66.95, H 6.21, N 16.44

Found: C 67.21, H 6.19, N 16.70.

EXAMPLE 12

To a suspension of 8.1 parts of 2-amino-7-chloro-5-phenyl-3H-1,4-benzodiazepine in 180 parts by volume of methanol are added 3.6 parts of 2-methylimidazole hydrochloride and 2.25 parts by volume of 80% hydrazine hydrate. The suspension is stirred at room temperature for 1.5 hours, and then 25 parts of ethyl orthoformate is added. To the mixture is added dropwise with stirring 60 parts by volume of ethanol containing 10% hydrogen chloride. After stirring for a further 1 hour, the mixture is warmed for a while so as to complete the reaction. After evaporation of the solvent, an aqueous solution of sodium bicarbonate is added to the residue to neutralize it. The mixture is then extracted with methylene chloride. The methylene chloride layer is washed with water and dried over sodium sulfate, followed by evaporation of the solvent. The residue is recrystallized from a mixture of acetone and n-hexane to give 8-chloro-6-phenyl-4H-s-triazolo [4,3-a][1,4] benzodiazepine as colorless flakes. Melting point; 226° C to 227° C.

Elementary analysis $C_{16}H_{11}ClN_4$: Calculated: C 65.20, H 3.76, N 19.01 Found: C 65.30, H 3.48, N 19.03.

EXAMPLE 13

To a solution of 2.8 parts of 7-chloro-2-hydrazino-5-phenyl-3H-1,4-benzodiazepine and 7.4 parts of ethyl orthoformate in 80 parts by volume of chloroform is added with stirring 2 parts of concentrated sulfuric acid. The mixture is stirred at room temperature for 30 minutes, followed by addition of saturated aqueous sodium bicarbonate to neutralize the mixture. The chloroform layer is washed with water and dried over anhydrous sodium sulfate, followed by evaporation of the solvent. The residue is recrystallized from a mixture of acetone and n-hexane to give 8-chloro-6-phenyl-4H-s-triazole [4,3-a][1,4] benzodiazepine as colorless flakes. Melting point: 226° C to 227° C.

Thus obtained product is identical with the product prepared in Example 12.

EXAMPLE 14

To a solution of 2.85 parts of 7-chloro-2-hydrazino-5-phenyl-3H-1,4-benzodiazepine in 100 parts by volume of methanol are added 7.4 parts of ethyl orthoformate and 20 parts by volume of methanol saturated with hydrogen chloride. The mixture is stirred for 2 hours and refluxed gently for 30 minutes. The solvent is distilled off under reduced pressure. To the residue is added saturated aqueous sodium bicarbonate so as to make the mixture alkaline, followed by extraction with chloroform. The chloroform extract is washed with water and dried over anhydrous sodium sulfate, followed by evaporation of the solvent. The residue is recrystallized from ethyl acetate to give 8-chloro-6-phenyl-4H-s-triazole [4,3-a][1,4] benzodiazepine as colorless flakes. Melting point: 226° C to 227°C.

Thus obtained product is identical with the product prepared in Examples 12 and 13.

Example 15

A solution of 2.8 parts of 7-chloro-2-hydrazino-5-phenyl-3H-1,4-benzodiazepine in 20 parts by volume of formic acid is left standing overnight. The solution is diluted with water, neutralized with an aqueous solution of sodium bicarbonate and extracted with chloroform. The chloroform extract is washed with water, dried over anhydrous sodium sulfate, and the solvent is evaporated. The residue is recrystallized from a mixture of acetone and n-hexane to give 8-chloro-6-phenyl-4H-s-triazolo [4,3-a][1,4] benzodiazepine as colorless flakes. Melting point: 226° C to 227° C.

Thus obtained product is identical with the product prepared in Exmples 12, 13 and 14.

EXAMPLE 16

To a suspension of 2.8 parts of 7-chloro-2-hydrazino 5-phenyl-3H-1,4-benzodiazepine in 40 parts by volume of formamide is added 1 part by volume of concentrated sulfuric acid. The resulting solution is left standing for 6 hours and then warmed on a boiling water bath for 30 minutes. The solution is diluted with water, neutralized with sodium bicarbonate and extracted with chloroform. The chloroform extract is washed with water and dried over anhydrous sodium sulfate, followed by evaporation of the solvent. The residue is recrystallized from ethyl acetate to give 8-chloro-6-phenyl-4H-s-triazolo [4,3-a][1,4] benzodiazepine as colorless flakes. Melting point: 226° C to 227° C.

Thus obtained product is identical with the product prepared in Examples 12, 13, 14 and 15.

EXAMPLE 17

A mixture of 2.8 parts of 7-chloro-2-hydrazino-5-phenyl-3H-1,4-benzodiazepine, 2.4 parts of formamidine hydrochloride and 2.5 parts of 2-methylimidazole is fused at 160° C for 10 minutes. Water is added to the mixture, followed by extraction with methylene chloride. The methylene chloride layer is washed with water, dried over sodium sulfate and the solvent is evaporated, whereby 8-chloro-6-phenyl-4H-s-triazolo [4,3-a][1,4] benzodiazepine is yielded. Recrystallization from ethyl acetate yields colorless flakes melting at 226° C to 227° C.

Thus obtained product is identical with the product prepared in Examples 12, 13, 14, 15 and 16.

EXAMPLE 18

To a suspension of 1.35 parts of 2-amino-7-chloro-5-phenyl-3H-1,4-benzodiazepine in 25 parts by volume of methanol are added 0.6 part of 2-methylimidazole hydrochloride and 6 parts by volume of 1 mole methanol solution of hydrazine hydrate. The mixture is stirred at room temperature for 1.5 hours, followed by addition of 4.8 parts of ethyl orthoacetate and 10 parts by volume of ethanol containing 10% hydrogen chloride. The mixture is refluxed for 30 minutes, followed by evaporation of the solvent. The residue is neutralized with saturated aqueous sodium bicarbonate and extracted with methylene chloride. The methylene chloride extract is washed with water and dried over sodium sulfate, followed by evaporation of the solvent. The residue is purified by means of silica gel column-chromatography to give 8-chloro-1-methyl-6-phenyl-4H-s-triazolo [4,3-a][1,4] benzodiazepine. Recrystallization from a mixture of acetone and n-hexane affords colorless needles. Melting point: 225° C to 226° C.

Elementary analysis $C_{17}H_{13}ClN_4$: Calculated: C 66.13, H 4.24, N 18.15 Found: C 66.39, H 4.08, N 18.07.

EXAMPLE 19

To a solution of 2.84 parts of 7-chloro-2-hydrazino-5-phenyl-3-H-1,4-benzodiazepine in 50 parts by volume of chloroform are added 10 parts of ethyl orthoacetate and 4 parts of p-toluenesulfonic acid. The solution is left standing at room temperature for 6 hours and heated for a while on a water-bath to complete the reaction. The mixture is washed with saturated aqueous sodium bicarbonate, then with water and dried over anhydrous sodium sulfate. After evaporation of the solvent, the residue is treated in a similar manner to Example 18 to give 8-chloro-1-methyl-6-phenyl-4H-s-triazolo [4,3-a][1,4] benzodiazepine as colorless needles. Melting point: 224° C to 225° C.

Thus obtained product is identical with the product prepared in Example 18.

Example 20

To a suspension of 2.84 parts of 7-chloro-2-hydrazino-5-phenyl-3H-1,4-benzodiazepine in 50 parts by volume of acetic anhydride is added 1 part by volume of concentrated sulfuric acid. The resulting solution is left standing at room temperature for 1 hour, poured in ice-water, neutralized with sodium bicarbonate and extracted with methylene chloride. The methylene chloride extract is washed with water and dried over anhydrous sodium sulfate, followed by evaporation of the solvent. The residue is recrystallized from a mixture of acetone and n-hexane to give 8-chloro-1-methyl-6-phenyl-4H-s-triazolo [4,3-a]][1,4] benzodiazepine as colorless needles. Melting point: 224° C to 225° C.

Thus obtained product is identical with the product prepared in Examples 18 and 19.

EXAMPLE 21

To a solution of 2.84 parts of 7-chloro-2-hydrazino-5-phenyl-3H-1,4-benzodiazepine in 60 parts by volume of chloroform is added 2.46 parts of ethyl acetoimidate hydrochloride. The mixture is stirred for 8 hours, and then aqueous sodium bicarbonate is added so as to neutralize the mixture. The chloroform layer is separated, washed with water and dried over anhydrous sodium sulfate, followed by evaporation of the solvent. The residue is recrystallized from ethyl acetate to give 8-chloro-1-methyl-6-phenyl-4H-s-triazolo [4,3-a] [1,4] benzodiazepine as colorless needles. Melting point: 225° C to 226° C.

Thus obtained product is identical with the product prepared in Examples 18, 19 and 20.

EXAMPLE 22

A mixture of 2.8 parts of 7-chloro-2-hydrazino-5-phenyl-3H-1,4-benzodiazepine, 2.8 parts of acetamidine hydrochloride and 2.5 parts of 2-methylimidazole is fused under heating at 160° C for 10 minutes. Water is added to the mixture, followed by extraction with methylene chloride. The methylene chloride layer is washed with water and dried over sodium sulfate. The solvent is evaporated, whereby 8-chloro-1-methyl-6-phenyl-4H-s-triazolo [4,3-a] [1,4] benzodiazepine is yielded. Recrystallization from ethyl acetate yields colorless needles melting at 223° C to 225° C.

Thus obtained product is identical with the product prepared in Examples 18, 19, 20 and 21.

EXAMPLE 23

A mixture of 2.8 parts of 7-chloro-2-hydrazino-5-phenyl-3H-1,4-benzodiazepine, 2.8 parts of acetamidine hydrochloride, 2.5 parts of 2-methylimidazole and 100 parts by volume of chloroform is stirred at room temperature for 24 hours. The chloroform layer is washed with water, dried over sodium sulfate and the solvent is evaporated. After treating the residue with diethyl ether, the resulting crystals are subjected to extraction with hot methanol. Evaporation of the methanol gives 2-(α-aminoethylidene) hydrazino-7-chloro-5-phenyl-3H-1,4-benzodiazepine as crystals. Recrystallization from acetone yields pale yellow needles melting at 203° C to 205° C (effervescence).

Elementary analysis $C_{17}H_{16}ClN_5$: Calculated: C 62.67, H 4.95, N 21.50 Found: C 62.99, H 4.84, N 21.53.

EXAMPLE 24

3.5 Parts of 2-(α-aminoethylidene) hydrazino-7-chloro-5-phenyl-3H-1,4-benzodiazepine prepared in Example 23 is heated on an oil bath at 200° C for 10 minutes, whereby it melts with foaming and then is solidified. Recrystallization from ethyl acetate yields 8-chloro-1-methyl-6-phenyl-4H-s-triazolo [4,3-a] [1,4] benzodiazepine as colorless needles melting at 225.5° C to 226.5° C.

Thus obtained product is identical with the product prepared in Examples 18, 19, 20, 21 and 22.

EXAMPLE 25

To a solution of 1.4 parts of 7-chloro-2-hydrazino-5-phenyl-3H-1,4-benzodiazepine in 30 parts by volume of chloroform is added with stirring 0.47 part by volume of acetic anhydride. The mixture is stirred for 1 hour and washed with a saturated aqueous solution of sodium bicarbonate and then with water. The chloroform layer is dried over sodium sulfate and the solvent is evaporated. Addition of methanol yields 2-(2-acetylhydrazino)-7-chloro-5-phenyl-3H-1,4-benzodiazepine as white crystals. Recrystallization from a mixture of chloroform and methanol yields powdery crystals melting at 202° C to 204° C (effervescence).

Elementary analysis $C_{17}H_{15}ClN_4O$: Calculated: C 62.48, H 4.63, N 17.15 Found: C 62.38, H 4.44, N 17.23.

EXAMPLE 26

3.3 Parts of 2-(2-acetylhydrazino)-7-chloro-5-phenyl-3H-1,4-benzodiazepine prepared in Example 25, is heated at 215° C for 10 minutes under mildly reduced pressure. The fused substance is recrystallized from ethyl acetate to yield 8-chloro-1-methyl-6-phenyl-4H-s-triazolo [4,3-a] [1,4] benzodiazepine as colorless needles melting at 225° C to 226° C.

Thus obtained product is identical with the product prepared in Examples 18, 19, 20, 21, 22 and 24.

EXAMPLE 27

A suspension of 3.3 parts of 2-(2-acetylhydrazino)-7-chloro-5-phenyl-3H-1,4-benzodiazepine prepared in Example 25 in 20 parts by volume of pyridine is refluxed, whereby the crystals are gradually dissolved. After 2 hours the solvent is evaporated under reduced pressure. The residue is recrystallized from a mixture of acetone and n-hexane to yield 8-chloro-1-methyl-6-phenyl-4H-s-triazolo [4,3-a] [1,4] benzodiazepine as colorless needles melting at 224° C to 225° C.

Thus obtained product is identical with the product prepared in Examples 18, 19, 20, 21, 22, 24 and 26.

EXAMPLE 28

To a mixture of 1.4 parts of 7-chloro-2-hydrazino-5-phenyl-3H-1,4-benzodiazepine prepared in Example 1, 50 parts by volume of ethanol and 4 parts by volume of ethyl orthopropionate is added 0.5 part by volume of concentrated sulfuric acid. The mixture is stirred for 30 minutes at room temperature and then treated in a similar manner to Example 14, whereby 8-chloro-1-ethyl-6-phenyl-4H-s-triazolo- [4,3-a] [1,4] benzodiazepine is yielded as crystals. Recrystallization from acetone yields colorless prisms melting at 229° C to 230° C.

Elementary analysis $C_{18}H_{15}ClN_4$: Calculated: C 66.97, H 4.68, N 17.36 Found: C 67.18, H 4.48, N 17.53.

EXAMPLE 29

To a solution of 1.4 parts of 7-chloro-2-hydrazino-5-phenyl-3H-1,4-benzodiazepine prepared in Example 1 in 30 parts by volume of chloroform is added with stirring 0.65 part by volume of propionic anhydride. The mixture is stirred for 1 hour, washed with a saturated aqueous solution of sodium bicarbonate, then with water, and dried over sodium sulfate. After evaporation of the chloroform, methanol is added to the residue, whereby 7-chloro-5-phenyl-2-(2-propionylhydrazino)-3H-1,4-benzodiazepine is yielded as crystals. Recrystallization from a mixture of chloroform and methanol yields colorless prisms melting at 186° C to 187° C (effervescence).

Elementary analysis $C_{18}H_{17}ClN_4O$: Calculated: C 63.43, H 5.03, N 16.44 Found: C 63.54, H 4.88, N 16.70.

EXAMPLE 30

Under mildly reduced pressure 3.4 parts of 7-chloro-5-phenyl-2-(2-propionylhydrazino)-3H-1,4-benzodiazepine prepared in Example 29 is heated at 195° C for 15 minutes. The fused substance is recrystallized from acetone to yield 8-chloro-1-ethyl-6-phenyl-4H-s-triazolo [4,3-a] [1,4] benzodiazepine as colorless prisms melting at 229° C to 230° C.

Thus obtained product is identical with the product prepared in Example 28.

EXAMPLE 31

To a mixture of 2.85 parts of 7-chloro-2-hydrazino-5-phenyl-3H-1,4-benzodiazepine, 50 parts by volume of chloroform and 2 parts by volume of triethylamine, a solution of 1.6 parts of enanthylchloride in 20 parts by volume of diethyl ether is gradually added with ice-cooling. The mixture is stirred for a while to complete the reaction. After evaporation of the solvent under reduced pressure, the residue is treated with methanol to yield 7-chloro-2-(2-enanthylhydrazino)-5-phenyl-3H-1,4-benzodiazepine as crystals. Recrystallization from a mixture of dimethylformamide and water yields colorless needles melting at 205° C to 206° C (effervescence).

Elementary analysis $C_{22}H_{25}ClN_4O$: Calculated: C 66.57, H 6.35, N 14.12 Found: C 66.43, H 6.24, N 14.29.

EXAMPLE 32

A mixture of 1.98 parts of 7-chloro-2-(2-enanthylhydrazino)-5-phenyl-3H-1,4-benzodiazepine and 30 parts of polyphosphoric acid is heated at 170° C to 180° C for 2 hours. To the mixture is added 200 parts by volume of ice-water and the resulting solution is neutralized with concentrated aqueous ammonia under ice-cooling, followed by extraction with chloroform. The chloroform layer is washed with water, dried over sodium sulfate and the solvent is evaporated. The residue is recrystallized from aqueous acetone to yield 8-chloro-1-hexyl-6-phenyl-4H-s-triazolo [4,3-a] [1,4] benzodiazepine as colorless plates melting at 75° C to 78° C (sintering).

Elementary analysis $C_{22}H_{23}ClN_4 \cdot 2H_2O$: Calculated: C 63.68, H 6.56, N 13.50 Found: C 63.71, H 6.15, N 13.60.

Thus obtained product is further dried under reduced pressure to yield the compound containing ¼$H_2O$ sintered at 61° C to 63° C.

EXAMPLE 33

A suspension of 4 parts of 7-chloro-2-(2-enanthylhydrazino)-5-phenyl-3H-1,4-benzodiazepine prepared in Example 31 in 20 parts by volume of pyridine is refluxed for about 3 hours. After evaporation of pyridine, water is added to the residue, whereby 8-chloro-1-hexyl-6-phenyl-4H-s-triazolo [4,3-a] [1,4] benzodiazepine is yielded as crystals. Recrystallization from aqueous acetone yields colorless flakes melting at 75° C to 78° C (sintering).

Thus obtained product is identical with the product prepared in Example 32.

EXAMPLE 34

To a solution of 1.4 parts of 7-chloro-2-hydrazino-5-phenyl-3H-1,4-benzodiazepine, prepared in Example 1, in 25 parts by volume of tetrahydrofuran is added 0.62 part by volume of benzoyl chloride, and the mixture is stirred at room temperature for 2 hours to complete the reaction. The reaction mixture is neutralized with a saturated aqueous solution of sodium bicarbonate. The resulting white precipitate is separated, washed with water and then with methanol, and dried, whereby 2-(2-benzoylhydrazino)-7-chloro-5-phenyl-3H-1,4-benzodiazepine is yielded as crystals. Recrystallization from a mixture of chloroform and methanol yields white needles melting at 207° C to 208° C (effervescence).

Elementary analysis $C_{22}H_{17}ClN_4O$: Calculated: C 67.95, H 4.41, N 14.41 Found: C 67.87, H 4.20, N 14.49.

EXAMPLE 35

A mixture of 38.8 parts of 2-(2-benzoylhydrazino)-7-chloro-5-phenyl-3H-1,4-benzodiazepine prepared in Example 34, and 400 parts of polyphosphoric acid is heated at 150° C for 1.5 hour. The mixture is treated in a similar manner to Example 32, whereby 8-chloro-1,6-diphenyl-4H-s-triazolo [4,3-a] [1,4] benzodiazepine is yielded as crystals. Recrystallization from ethyl acetate yields colorless needles melting at 191° C to 192° C.

Elementary analysis $C_{22}H_{15}ClN_4$: Calculated: C 71.25, H 4.08, N 15.11 Found: C 71.11, H 4.10, N 14.98.

EXAMPLE 36

Under mildly reduced pressure 3.9 parts of 2-(2-benzoylhydrazino)-7-chloro-5-phenyl-3H-1,4-benzodiazepine prepared in Example 34 is fused under heating at 215° C for about 15 minutes until foaming is ceased. Recrystallization of the fused substance from ethyl acetate yields 8-chloro-1,6-diphenyl-4H-s-triazolo [4,3-a] [1,4] benzodiazepine as colorless needles melting at 193° C to 194° C.

Thus obtained product is identical with the product prepared in Example 35.

EXAMPLE 37

A solution of 1.4 parts of 7-chloro-2-hydrazino-5-phenyl-3H-1,4-benzodiazepine and 1.8 parts of ethyl benzimidate hydrochloride in 30 parts by volume of chloroform is stirred at room temperature for 24 hours and then washed with water. The chloroform layer is dried over sodium sulfate and the solvent is evaporated. Treatment of the residue with diethyl ether yields 8-chloro-1,6-diphenyl-4H-s-triazolo-[4,3-a] [1,4] benzodiazepine as crystals. Recrystallisation from a mixture of ethyl acetate and n-hexane yields colorless needles melting at 192° C to 193.5° C.

Thus obtained product is identical with the product prepared in Examples 35 and 36.

EXAMPLE 38

In a similar manner to Example 31, a solution of 0.85 part of phenylacetyl chloride in 10 parts by volume of diethyl ether is added to a mixture of 1.4 parts of 7-chloro-2-hydrazino-5-phenyl-3H-1,4-benzodiazepine, 1 part by volume of triethylamine and 25 parts by volume of chloroform. The whole mixture is stirred for 45 minutes, whereby 7-chloro-2-(2-phenylacetylhydrazino)-5-phenyl-3H-1,4-benzodiazepine is yielded as crystals. Recrystallization from a mixture of dimethylformamide and water yields colorless fine prisms melting at 220° C to 221° C (effervescence).

Elementary analysis $C_{23}H_{19}ClN_4O$: Calculated: C 68.57, H 4.75, N 13.91 Found: C 68.72, H 4.79, N 13.71.

EXAMPLE 39

A mixture of 4 parts of 7-chloro-2-(2-phenylacetylhydrazino)-5-phenyl-3H-1,4-benzodiazepine prepared in Example 38, and 50 parts of polyphosphoric acid is heated at 180° C for 2 hours. The mixture is treated in a similar manner to Example 32 and 35, whereby 1-benzyl-8-chloro-6-phenyl-4H-s-triazolo [4,3-a] [1,4] benzodiazepine is yielded. Recrystallization from ethyl acetate yields colorless pillars melting at 190° C to 192° C.

Elementary analysis $C_{23}H_{17}ClN_4$ Calculated: C 71.78, H 4,45, N 14.56 Found: C 72.07, H 4.34, N 14.74.

Recrystallization from methanol yields colorless needles melting at 101° C to 103° C (effervescence).

Elementary analysis $C_{23}H_{17}ClN_4 \cdot CH_3OH$: Calculated: C 69.14, H 5.08, N 13.44 Found: C 69.31, H 5.02, N 13.59.

EXAMPLE 40

4 Parts of 7-chloro-2-(2-phenylacetylhydrazino)-5-phenyl-3H-1,4-benzodiazepine prepared in Example 38, is fused under heating at 230° C for 10 minutes under mildly reduced pressure until foaming is ceased. Recrystallization of the fused substance from ethyl acetate yields 1-benzyl-8-chloro- 6-phenyl-4H-s-Triazolo [4,3-a] [1,4] benzodiazepine as colorless prisms melting at 191° C to 192° C.

Thus obtained product is identical with the product prepared in Example 39.

EXAMPLE 41

To a suspension of 1.6 parts of 7-chloro-2-hydrazino-5-(p-methoxyphenyl)-3H-1,4-benzodiazepine prepared in Example 2 in 50 parts by volume of ethanol is added 3.0 parts of ethyl orthoformate, and then 0.5 part by volume of concentrated sulfuric acid is added dropwise with stirring. The whole mixture is stirred for a while and then neutralized with an aqueous slution of sodium bicarbonate, followed by evaporaton of the solvent. Water is added to the residue, whereby 8-chloro-6-(p-methoxyphenyl)-4H-s-triazolo (4,3-a) (1,4) benzodiazepine is yielded as crystals. Recrystallization from acetone and and then from ethyl acetate yields pale yellow flakes melting at 216° C to 217° C.

Elementary analysis $C_{17}H_{13}ClN_4O$: Calculated: C 62.87, H 4.03, N 17.25 Found: C 62.98, H 3.95, N 17.57

Example 42

To a mixture of 2.1 parts of 7-chloro-2-hydrazino-5-(p-methoxyphenyl)-3H-1,4-benzodiazepine, prepared in Example 2, 4.33 parts of ethyl orthoacetate and 60 parts by volume of ethanol is added dropwise 0.75 part by volume of concentrated sulfuric acid. The mixture is stirred for about 15 minutes. After completion of the reaction, the reaaction mixture is neutralized with a saturated aqueous solution of sodium bicarbonate, whereby 8-chloro-1-methyl-6-(p-methoxyphenyl)-4H-s-triazolo [4,3-a] [1,4] benzodiazepine is yielded as crystals. Recrystallization from a mixture of methanol and chloroform yields colorless needles melting at 268° C to 269° C.

Elementary analysis $C_{18}H_{15}ClN_4O$: Calculated: C 63.81, H 4.46, N 16.54 Found: C 63.76, H 4.31, N 16.58.

EXAMPLE 43

To a mixture of 1 part of 2-hydrazino-5-phenyl-3H-1,4-benzodiazepine, prepared in Example 3, 2 parts by volume of ethyl orthoformate and 20 parts by volume of ethanol, 0.44 part by volume of concentrated sulfuric acid is added dropwise with ice-cooling. The mixture is stirred at room temperature for 30 minutes and neutralized with saturated aqueous sodium bicarbonate. The resulting oily substance is extracted with methylene chloride. The methylene chloride layer is washed with water, dried over sodium sulfate and the solvent is evaporated, whereby 6-phenyl-4H-s-triazolo [4,3-a] [1,4] benzodiazepine is yielded as crystals. Recrystallization from a mixture of acetone and n-hexane yields colorless needles melting at 195° C to 196° C.

Elementary analysis $C_{16}H_{12}N_4$: Calculated: C 73.83, H 4.65, N 21.53 Found: C 73.71, H 4.37, N 21.21.

The compound may be obtained as polymorpholic pillars melting at 201° C to 202° C by recrystalliation from the same solvent and its elementary analytical data coincides with the calculated value for $C_{16}H_{12}N_4$.

EXAMPLE 44

The same procedure as in Example 43 is repeated except that 4 parts by volume of ethyl orthoacetate is employed in place of ethyl orthoformate, whereby 1-methyl-6-phenyl-4H-s-triazolo [4,3-a] [1,4] benzodiazepine is yielded. Recrystallization from a mixture of methanol and ethyl acetate yields colorless prisms melting at 226° C to 227° C.

Elementary analysis $C_{17}H_{14}N_4$; Calculated: C 74.43, H 5.14, N 20.43: Found: C 74.70, H 5.17, N 20.41.

Example 45

To a mixture of 3.2 parts of 2-hydrazino-5-phenyl-7-trifluoromethyl-3H-1,4-benzodiazepine, prepared in Example 4, 8.5 parts of ethyl orthoformate and 50 parts by volume of chloroform, is added dropwise 7.6 parts of p-toluenesulfonic acid at a temperature below 10° C. The mixture is stirred at room temperature for 2.5 hours. After completion of the reaction, the reaction mixture is neutralized with a saturated aqueous solution of sodium bicarbonate. The chloroform layer is separated, washed with water and dried over sodium sulfate. Evaporation of the solvent yields 6-phenyl-8-trifluoromethyl-4H-s-triazolo [4,3-a] [1,4] benzodiazepine as crystals. The crystals are dissolved in ethanol and the insoluble material is removed by filtration. The filtrate is concentrated and recrystallized from ethyl acetate to give colorless flakes. Melting point: 258° C to 260° C.

Elementary analysis $C_{17}H_{11}F_3N_4$: Calculated: C 62.19, H 3.38, N 17.07 Found: C 61.99, H 3.46, n 16.89.

EXAMPLE 46

To a mixture of 9,5 parts of 2-hydrazino-5-phenyl-7-trifluoromethyl-3-H-1,4-benzodiazepine prepared in Example 4, 29 parts of ethyl orthoacetate and 150 parts by volume of chloroform, is added dropwise 23 parts of p-toluenesulfonic acid with stirring under ice-cooling below 10° C and then the mixture is stirred at room temperature for 7 hours. After completion of the reaction, the reaction mixture is neutralized with a saturated aqueous solution of sodium bicarbonate and the chloroform layer is separated, washed with water and dried over sodium sulfate. After evaporation of the solvent, the residue is treated with a mixture of benzene and isopropyl ether, whereby 1-methyl-6-phenyl-8-trifluoromethyl-4H-s-triazolo [4,3-a] [1,4] benzodiazepine is yielded as crystals containing benzene of crystallization. Recrystallization from a mixture of benzene and n-hexane yields colorless needless melting at 129° C to 130° C (sintering), 133° C to 134° C (effervescence).

Elementary analysis $C_{18}H_{13}F_3N_4 \cdot \frac{1}{2}C_6H_6$: Calculated: C 65.21, H 4.10, N 15.21 Found: C 65.26, H 4.20, N 14.81.

Recrystallization from aqueous acetone yields colorless needles containing $1/5H_2O$ and melting at 112° C to 113° C (sintering).

Elementary analysis $C_{18}H_{13}F_3N_4 \cdot 1/5H_2O$: Calculated: C 62.49, H 3.90, N 16.20 Found: C 62.53; H 4.08, N 16.42

EXAMPLE 47

To a mixture of 5.3 parts of 2-hydrazino-7-methyl-5-phenyl-3H-1,4-benzodiazepine prepared in Example 5, 14.8 parts of ethyl orthoformate and 150 parts by volume of ethanol, is added dropwise 4 parts of fconcentrated sulfuric acid under cooling. The whole mixture is stirred for about 30 minutes and neutralized with a saturated aqueous solution of sodium bicarbonate, followed by extraction with chloroform. The chloroform layer is washed with water and dried over sodium sulfate. After evaporation of the solvent, the residue is treated with n-hexane, whereby 8-methyl-6-phenyl-4H-s-triazolo [4,3-a][1,4] benzodiazepine is yielded as crystals. Recrystallization from ethyl acetate yields pale yellow prisms melting at 177° C to 178° C.

Elementary analysis $C_{17}H_{14}N_4$: Calculated: C 74.43, H 5.14, N 20.43 Found: C 74.30, H 5.15, N 20.14.

EXAMPLE 48

The same procedure as Example 47 is repeated except that 16.2 parts of ethyl orthoacetate is employed in place of ethyl orthoformate, whereby 1,8-dimethyl-6-phenyl-4H-s-triazolo [4,3-a][1,4] benzodiazepine is yielded as crystals. Recrystallization from ethyl acetate yields colorless needles melting at 211° C to 211.5° C.

Elementary analysis $C_{18}H_{16}N_4$: Calculated: C 74.97, H 5.59, N 19.43 Found: C 74.93, H 5.42, N 19.73.

EXAMPLE 49

To a mixture of 2.8 parts of 2-hydrazino-7-methoxy-5-phenyl-3H-1,3-benzodiazepine prepared in Example 6, 7.4 parts of ethyl orthoformate and 100 parts by volume of ethanol, is added 2 parts of concentrated sulfuric acid with stirring and ice-cooling. The mixture is stirred at room temperature for about 45 minutes to complete the reaction. After evaporation of the solvent under reduced pressure, the residue is neutralized with a saturated aqueous solution of sodium bicarbonate, followed by extraction with chloroform. The chloroform layer is washed with water and dried over sodium sulfate. Evaporation of the solvent under reduced pressure leaves 8-methoxy-6-phenyl-4H-s-triazolo [4,3-a][1,4] benzodiazepine as crystals. Recrystallization from ethyl acetate yields pale yellow prisms melting at 209° C to 210° C.

Elementary analysis $C_{17}H_{14}N_4O$: Calculated: C 70.33, H 4.86, N 19.30 Found: C 70.23, H 4.93, N 19.15.

EXAMPLE 50

The same procedure as Example 49 is repeated except that 8 parts of ethyl orthoacetate is employed in place of the ethyl orthoformate, whereby 1-methyl-8-methoxy-6-phenyl-4H-s-triazolo [4,3-a][1,4] benzodiazepine is yielded as crystals. Recrystallization from ethyl acetate yields pale yellow prisms melting at 196° C to 197° C.

Elementary analysis $C_{18}H_{16}N_4O$: Calculated: C 71.03, H 5.30, N 18.41 Found: C 71.16, H 5.44, N 18.21.

EXAMPLE 51

2-Hydrazino-7-nitro-5-phenyl-3H-1,4-benzodiazepine prepared from 5.6 parts of 2-amino-7-nitro-5-phenyl-3H-1,4-benzodiazepine in a similar manner to Example 7, is dissolved in a mixture of 20 parts by volume of ethyl orthoformate and 100 parts by volume of chloroform, followed by the addition of 10 parts of p-toluenesulfonic acid. The whole mixture is left standing at room temperature for 1 hour with occasional shaking. After completion of the reaction, the solution is washed with a saturated aqueous solution of sodium bicarbonate, then with water, and dried over sodium sulfate. After evaporation of the solvent, the residue is treated with ethyl acetate, whereby 8-nitro-6-phenyl-4H-s-triazolo [4,3-a][1,4] benzodiazepine is yielded as crystals. Recrystallization from tetrahydrofuran yields pale yellow needles melting at 271° C to 272° C.

Elementary analysis $C_{16}H_{11}N_5O_2$ Calculated: C 62.94, H 3.63; N 22.94 Found: C 63.07, H 3.75, N 23.39:

EXAMPLE 52

The same procedure as Example 51 is repeated except that 20 parts by volume of ethyl orthoacetate is employed in place of the ethyl orthoformate, whereby 1-methyl-8-nitro-6-phenyl-4H-s-triazolo [4,3-a][1,4] benzodiazepine is yielded as yellow crystals. Recrystallization from acetone yields yellow prisms melting at 227° C to 229° C.

Elementary analysis C 62.094, H 3.63, N 22.94 Found: C 63.07, H 3.75, N 23.39:

EXAMPLE 52

The same procedure as Example 51 is repeated except that 20 parts by volume of ethyl orthoacetate is employed in place of the ethyl orthoformate, whereby 1-methyl-8-nitro-6-phenyl-4H-s-triazolo [4,3-a][1,4] benzodiazepine is yielded as yellow crystals. Recrystallization from acetone yields yellow prisms melting at 227° C to 229° C.

Elementary analysis $C_{17}H_{13}N_5O_2$: Calculated: C 63.94, H 4.10, N 21.93 Found: C 64.11, H 4.00, N 21.69.

EXAMPLE 53

To a mixture of 1.7 parts of 7-chloro-2-hydrazino-3-isobutyl-5-phenyl-3H-1,4-benzodiazepine prepared in Examples 8 and 11, 3.7 parts of triethyl orthoformate and 40 parts by volume of ethanol, is added 1 part of concentrated sulfuric acid with stirring and ice-cooling.

The mixture is stirred for about 20 minutes at room temperature. After completion of reaction, the mixture is neutralized with sodium bicarbonate, followed by extraction with chloroform. The chloroform layer is washed with water and dried over sodium sulfate. After evaporation of the solvent, the residue is treated with n-hexane, whereby 8-chloro-4-isobutyl-6-phenyl-4H-s-triazolo [4,3-a][1,4] benzodiazepine is yielded as pale yellow crystals. Recrystallization from a mixture of benzene and n-hexane yields colorless needles melting at 140.5° C to 141.5° C.

Elementary analysis C$_{20}$H$_{19}$ClN$_4$: Calculated: C 68.47, H 5.46, N 15.97 Found: C 68.56, H 5.30, N 16.11

EXAMPLE 54

To a suspension of 14.3 parts of 2-amino-7-chloro-5-phenyl-3H-1,4-benzodiazepine 4N-oxide in 400 parts by volume of methanol are added 12.5 parts by volume of 100% hydrazine hydrate and 10 parts by volume of methanol saturated with hydrogen chloride. The mixture is refluxed for 10 minutes and the resulting solution is concentrated to half the initial volume. The concentrate is poured into 500 parts by volume of water and the resulting oily substance is extracted with chloroform. The chloroform layer is dried over sodium sulfate and evaporated. Treatment of the residue with diethyl ether gives 7-chloro-2-hydrazino-5-phenyl-3H-1,4-benzodiazepine 4N-oxide as pale yellow powdery crystals melting at 262° C to 263° C.

Elementary analysis C$_{15}$H$_{13}$ClN$_4$O: Calculated: C 59.90, H 4.36, N 18.63 Found: C 60.05, H 4.13, N 18.41.

EXAMPLE 55

To a solution of 3 parts of 7-chloro-2-hydrazino-5-phenyl-3H-1,4-benzodiazepine 4N-oxide, prepared in Example 54, in 60 parts by volume of chloroform is added 7.4 parts of ethyl orthoformate and then 1.1 parts by volume of concentrated sulfuric acid is added dropwise. The whole mixture is stirred for about 20 minutes, followed by neutralization with saturated aqueous sodium bicarbonate. The chloroform layer is washed and dried over sodium sulfate. Evaporation of the solvent leaves 8-chloro-6-phenyl-4H-s-triazolo [4,3-][1,4] benzodiazepine 5N-oxide as crystals. Recrystallization from a mixture of methanol and chloroform (1:1 by volume) yields colorless needles melting at 267° C to 268° C (decomposition).

Elementary analysis C$_{16}$H$_{11}$ClN$_4$O: Calculated: C 61.74, H 3.57, N 18.03 Found: C 61.87, H 3.26, N 17.92.

EXAMPLE 56

To a mixture of 3 parts of 7-chloro-2-hydrazino-5-phenyl-3H-1,4-benzodiazepine 4N-oxide, and 20 parts by volume of formamide, is added dropwise 1.1 parts by volume of concentrated sulfuric acid and the whole mixture is stirred for about 4 hours. After completion of the reaction, the mixture is neutralized with a saturated aqueous solution of sodium bicarbonate. The resulting crystals of 8-chloro-6-phenyl-4H-s-triazolo [4,3-a][1,4] benzodiazepine 5N-oxide are separated by filtration and recrystallized from chloroform to give colorless needles melting at 267° C to 269° C (decomposition).

Thus obtained product is identical with the product prepared in Example 55.

EXAMPLE 57

A solution of 3 parts of 7-chloro-2-hydrazino-5-phenyl-3H-1,4-benzodiazepine 4N-oxide in 20 parts by volume of 99% formic acid is allowed to stand overnight at room temperature and the solvent is distilled off. Neutralization with saturated aqueous sodium bicarbonate yields 8-chloro-6-phenyl-4H-s-triazolo [4,3-a][1,4] benzodiazepine 5N-oxide as crystals. Recrystallization from chloroform yields colorless crystals melting at 268° C to 269° C (decomposition).

Thus obtained product is identical with the product prepared in Examples 55 and 56.

EXAMPLE 58

To a suspension of 3 parts of 7-chloro-2-hydrazino-5-phenyl-3H-1,4-benzodiazepine 4N-oxide, prepared in Example 54, and 8 parts of ethyl orthoacetate in 100 parts by volume of ethanol, is added dropwise 1.1 parts by volume of concentrated sulfuric acid. The whole mixture is stirred for about 15 minutes at room temperature, followed by evaporation of the solvent. The residue is neutralized with saturated aqueous sodium bicarbonate, whereby 8-chloro-1-methyl-6-phenyl-4H-s-triazolo [4,3-a][1,4] benzodiazepine 5N-oxide is obtained as crystals. Recrystallization from a mixture of methanol and dimethyl ether yields colorless needles melting at 272° C to 273° C (decomposition).

Elementary analysis C$_{17}$H$_{13}$ClN$_4$O: Calculated: C 62.87, H 4.03, N 17.25 Found: C 63.04, H 4.04, N 17.26.

EXAMPLE 59

To a solution of 3 parts of 7-chloro-2-hydrazino-5-phenyl-3,4-1,4-benzodiazepine 4N-oxide in 100 parts by volume of ethanol, is added 2.5 parts of ethyl acetoimidate hydrochloride. The mixture is refluxed for about 30 minutes, followed by evaporation of the solvent. The residue is neutralized with a saturated aqueous solution of sodium bicarbonated, whereby 8-chloro-1-methyl-6-phenyl-4H-s-triazolo [4,3-a][1,4] benzodiazepine 5N-oxide is obtained as crystals. Recrystallization from a mixture of methanol and diethyl ether yields colorless needles melting at 268° C to 269° C. (decomposition).

Thus obtained product is identical with the product prepared in Example 58.

EXAMPLE 60

A mixture of 3 parts of 7-chloro-2-hydrazino-5-phenyl-3H-1,4-benzodiazepine 4N-oxide, 4 parts of acetamidine hydrochloride and 5 parts of 2-methylimidazole is fused under heating at 175° C for 10 minutes. After cooling, water is added to the mixture, followed by extraction with chloroform. The chloroform layer is washed with water and dried over sodium sulfate. Evaporation of the solvent, followed by addition of methanol to the residue yields 8-chloro-1-methyl-6-phenyl-4H-s-triazolo [4,3-a][1,4] benzodiazepine 5N-oxide as crystals. Recrystallization from methanol yields colorless needles melting at 268° C to 270° C. (decomposition).

Thus obtained product is identical with the product prepared in Examples 58 and 59.

EXAMPLE 61

To a mixture of 1.5 parts of 7-chloro-2-hydrazino-5-phenyl- 3H-1,4-benzodiazepine 4N-oxide, 50 parts by volume of tetrahydrofuran and 1 part by volume of triethylamine, is added 0.5 part by volume of acetic anhydride with stirring. The whole mixture is stirred for about 1 hour, followed by the addition of water, whereby 2-(2-acetylhydrazino)-7-chloro-5-phenyl-3H-1,4-benzodiazepine 4N-oxide is yielded as crystals. Recrystallization from a mixture of dimethylformamide and water yields fine needles melting at 256° C to 258° C (decomposition).

Elementary analysis $C_{17}H_{15}ClN_4O_2$: Calculated: C 59.56, H 4.41, N 16.35, Found: C 59.38, H 4.55, N 16.30.

EXAMPLE 62

A mixture of 3.4 parts of 2-(2-acetylhydrazino)-7-chloro-5-phenyl-3H-1,4-benzodiazepine 4N-oxide, prepared in Example 61, and 30 parts by volume of pyridine is refluxed for 4 hours, followed by evaporation of the pyridine under reduced pressure. The residue is recrystallized from methanol, whereby 8-chloro-1-methyl-6-phenyl-4H-s-triazolo[(4,3-a][1,4] benzodiazepine 5N-oxide is yielded as needles melting at 272° C to 274° C (decomposition).

Thus obtained product is identical with the product prepared in Examples 58, 59 and 60.

EXAMPLE 63

To a suspension of 3 parts of 7-chloro-2-hydrazino-5-phenyl-3H-1,4-benzodiazepine 4N-oxide, prepared in Example 54, and 8.8 parts of ethyl orthopropionate in 100 parts by volume of ethanol is added dropwise 1.1 parts by volume of concentrated sulfuric acid. The whole mixture is stirred for 20 minutes, followed by evaporation of the solvent. The residue is neutralized with a saturated aqueous solution of sodium bicarbonate, whereby 8-chloro-1-ethyl-6-phenyl-4H-s-triazolo [4,3-a][1,4] benzodiazepine 5N-oxide is crystallized out. Recrystallization from methanol yields colorless flakes melting at 273° C to 274° C (decomposition).

Elementary analysis $C_{18}H_{15}ClN_4O$: Calculated: C, 63.81, H, 4.46, N, 16.54. Found: C, 63.60, H, 4.20, N, 16.34.

EXAMPLE 64

To a mixture of 3 parts of 2-amino-7-nitro-5-phenyl-3H-1,4-benzodiazepine 4N-oxide and 100 parts by volume of ethanol are added 2.5 parts by volume of 100% hydrazine hydrate and 1.8 parts by volume of acetic acid. The whole mixture is slightly warmed on a water bath for a while to make a solution and stirred aat room temperature for about 20 minutes. The precipitated crystals are collected, and washed with ethanol and then with diethyl ether, whereby 2-hydrazino-7-nitro-5-phenyl-3H-1,4-benzodiazepine 4N-oxide is yielded as yellow needles melting at 176° C (sintering), 226° C (decomposition).

Elementary analysis $C_{15}H_{13}N_5O_3$: Calculated C 57.87, H 4.21, N 22.50 Found: C 57.98, H 4.01, N 22.26

EXAMPLE 65

To a suspension of 1.55 parts of 2-hydrazino-7-nitro-5-phenyl-3H-1,4-benzodiazepine 4N-oxide, prepared in Example 64, in 100 parts by volume of ethanol, is added 3.7 parts of ethyl orthoformate, and then 0.6 part by volume of concentrated sulfuric acid, whereby the solid substance is once dissolved and then yellow crystals are precipitated. After stirring for 30 minutes, the mixture is neutralized with a saturated aqueous solution of sodium bicarbonate. The crystals are collected and washed with water, ethanol and then diethyl ether, whereby 8-nitro-6-phenyl-4H-s-triazolo [4,3-a][1,4] benzodiazepine 5N-oxide is yielded as yellow crystals. Recrystallization from an aqueous dimethylformamide yields yellow crystals melting at 274° C to 275° C (decomposition).

Elementary analysis $C_{16}H_{11}N_5O_3$: Calculated: C 59.81, H 3.45, N 21.80 Found: C 59.58, H 3.48, N 21.56.

EXAMPLE 66

A mixture of 3.1 parts of 8-chloro-6-phenyl-4H-s-triazolo [4,3-a][1,4] benzodiazepine 5N-oxide, prepared in Examples 55, 56 and 57, 200 parts by volume of chloroform and 5.3 parts by volume of phosphorus trichloride is refluxed for 1 hour. After evaporation of the solvent, saturated aqueous sodium bicarbonate is added to the residue, followed by extraction with chloroform. The chloroform layer is washed with water and dried over sodium sulfate. Evaporation of the solvent leaves 8-chloro-6-phenyl-4H-s-tiazolo [4,3-a][1,4] benzodiazepine as crystals. Recrystallization from ethyl acetate yields colorless flakes melting at 223.5° C to 224.5° C.

Thus obtained product is identical with the product prepared in Examples 12, 13, 14, 15, 16 and 17.

EXAMPLE 67

To 200 parts by volume of methanol are added 3.1 parts of 8-chloro-6-phenyl-4H-s-triazolo [4,3-a][1,4] benzodiazepine 5N-oxide and 1 part by volume of Raney nickel. The mixture is subjected to catalytic hydrogenation. After absorption of 1 mole equivalent of hydrogen, the catalyst is removed by filtration and the filtrate is concentrated to dryness. Recrystallization of the residue from ethyl acetate yields 8-chloro-6-phenyl-4H-s-triazolo [4,3-a][1,4] benzodiazepine as colorless flakes melting at 222° C to 223° C.

Thus obtained product is identical with the product prepared in Example 66.

EXAMPLE 68

A mixture of 3.4 parts of 8-chloro-1-ethyl-6-phenyl-4H-s-triazolo [4,3-a][1,4] benzodiazepine 5N-oxide, prepared in Example 63, 200 parts by volume of chloroform and 5.3 parts by volume of phosphorus trichloride is refluxed for 1.5 hours and then the solvent is evaporated. The residue is neutralized with a saturated aqueous solution of sodium bicarbonate and extracted with chloroform. The chloroform layer is washed with water and dried over sodium sulfate. After evaporation of the solvent, the residue is treated with a mixture of acetone and petroleum ether, whereby 8-chloro-1-ethyl-6-phenyl-4H-s-triazolo [4,3-a][1,4] benzodiazepine is obtained as crystals. Recrystallization from acetone yields colorless granules melting at 229° C to 230° C.

Thus obtained product is identical with the product prepared in Examples 28 and 30.

EXAMPLE 69

To a suspension of 3.2 parts of 8-nitro-6-phenyl-4H-s-triazolo [4,3-a][1,4] benzodiazepine 5N-oxide in 600 parts by volume of chloroform, is added 20 parts by volume of phosphorus trichloride. The mixture is refluxed for 16 hours, followed by evaporation of the solvent. The residue is neutralized with a saturated aqueous solution of sodium bicarbonate and extrated with chloroform. The chloroform layer is washed with water, dried over sodium sulfate. After evaporation of the solvent, the residue is treated with ethanol, whereby 8-nitro-6-phenyl-4H-s-triazolo [4,3-a][1,4] benzodiazepine is yielded as crystals. Recrystallization from tetrahydrofuran yields pale yellow needles melting at 266° C to 267° C.

Thus obtained product is identical with the product prepared in Example 51.

EXAMPLE 70

To a solution of 1.43 parts of 7-chloro-5phenyl-3-H-1,4-benzodiazepine-2-thione in 12.5 parts by volume of 0.4 N sodium methoxide in methanol is added dropwise with stirring 0.6 part by volume of benzyl bromide and the stirring is continued for an additional 30 minutes. Water is added to the reaction mixture and the resulting oil is extracted with ethyl acetate. The ethyl acetate layer is washed with water and dried over sodium sulfate. Evaporation of the solvent yields 2-benzylmercapto-7-chloro-5-phenyl-3H-1,4-benzodiazepine as an oil.

Thus obtained 2-benzylmercapto-7-chloro-5-phenyl-3H-1,4-benzodiazepine (4 parts) is dissolved in 100 parts by volume of a mixture of methanol and tetrahydrofuran (1:1) and 10 parts by volume of hydrazine hydrate is added thereto. After being left standing overnight at room temperature, the reaction mixture is poured into water and extracted with chloroform. The chloroform layer is washed with water and dried over sodium sulfate. Evaporation of the solvent affords 7-chloro-2-hydrazino-5-phenyl-3H-1,4-benzodiazepine. Recrystallization from a mixture of chloroform and benzene gives colorless crystals. M.P. 203°–205° C (decomposition). Thus obtained product is identical with the product prepared in Examples 1 and 9.

What is claimed is:

1. A compound of the formula

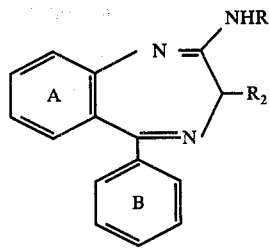

wherein R is

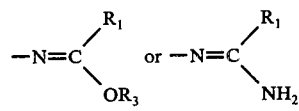

in which $R_1$ is hydrogen, alkyl of 1-6 carbon atoms, benzyl, phenethyl or phenyl and $R_3$ is methyl or ethyl, the rings A and B, independently of each other, are each unsubstituted or substituted by one member selected from the group consisting of nitro, halogen, trifluoromethyl, methyl, ethyl, propyl, methoxy and ethoxy, $R_2$ is hydrogen, methyl, ethyl, propyl, iso-propyl, butyl, sec-butyl, tert-butyl, amyl or hexyl, and the nitrogen atom at the 4-position is optionally in the form of an N-oxide.

2. The compound as claimed in claim 1, namely 2-(α-aminoethylidene)hydrazino-7-chloro-5-phenyl-3H-1,4-benzodiazepine.

* * * * *